United States Patent [19]

Reuter

[11] Patent Number: 5,770,087

[45] Date of Patent: Jun. 23, 1998

[54] CONTINUOUS CHROMATOGRAPHY

[76] Inventor: Karl Arnold Reuter, Sundgauallee 88, D-79110 Freiburg, Germany

[21] Appl. No.: 709,878

[22] Filed: Sep. 9, 1996

Related U.S. Application Data

[63] Continuation of Ser. No. 476,057, Jun. 7, 1995, abandoned, which is a continuation of Ser. No. 119,082, Sep. 16, 1993, abandoned.

[30] Foreign Application Priority Data

Mar. 18, 1991 [DE] Germany .......................... 41 08 820.4

[51] Int. Cl.$^6$ ................................ C02F 1/28; C02F 1/42
[52] U.S. Cl. ...................... 210/657; 210/660; 210/198.2; 210/321.68
[58] Field of Search .............................. 210/650, 321.63, 210/656, 634, 660, 321.68, 657, 198.2, 198.3

[56] References Cited

U.S. PATENT DOCUMENTS

| | | | |
|---|---|---|---|
| 3,355,382 | 11/1967 | Huntington | 210/321.68 |
| 3,417,548 | 12/1968 | Thompson | 55/67 |
| 3,503,712 | 3/1970 | Sussman | 23/252 |
| 3,511,028 | 5/1970 | Saylor | 55/67 |
| 3,578,757 | 5/1971 | Samuilov et al. | 55/197 |
| 3,797,662 | 3/1974 | Titus | 210/360 |
| 4,066,554 | 1/1978 | Guyer | 210/342 |
| 4,093,552 | 6/1978 | Guyer | 210/298 |
| 4,104,038 | 8/1978 | Josis | 55/19 |
| 4,150,957 | 4/1979 | Josis | 55/53 |
| 4,287,061 | 9/1981 | Sutherland | 210/198.2 |
| 4,321,138 | 3/1982 | Ito | 210/657 |
| 4,427,552 | 1/1984 | Lieberherr et al. | 210/741 |
| 4,726,903 | 2/1988 | Dickey | 210/635 |
| 4,740,310 | 4/1988 | Dickey | 210/649 |
| 4,790,942 | 12/1988 | Shmidt et al. | 210/650 |
| 4,867,878 | 9/1989 | Rashev | 210/363 |
| 4,871,462 | 10/1989 | Fischel et al. | 210/321.68 |
| 4,874,507 | 10/1989 | Whitlock | 209/11 |
| 4,876,013 | 10/1989 | Shmidt et al. | 210/650 |
| 4,900,440 | 2/1990 | Ziegler et al. | 210/321.68 |
| 4,906,379 | 3/1990 | Hodgins et al. | 210/638 |
| 4,911,847 | 3/1990 | Shmidt et al. | 210/650 |
| 5,000,848 | 3/1991 | Hodgins et al. | 210/321.68 |
| 5,024,758 | 6/1991 | Ito | 210/198.2 |
| 5,130,001 | 7/1992 | Snyder et al. | 210/657 |
| 5,186,824 | 2/1993 | Anderson et al. | 210/657 |
| 5,194,145 | 3/1993 | Schoendorfer | 210/321.68 |
| 5,254,248 | 10/1993 | Nakamura | 210/321.67 |
| 5,272,075 | 12/1993 | Anderson et al. | 435/183 |
| 5,273,656 | 12/1993 | Anderson et al. | 210/635 |

FOREIGN PATENT DOCUMENTS

| | | |
|---|---|---|
| 433510 | 12/1969 | Australia . |
| 168140 | 1/1986 | European Pat. Off. . |
| 1043354 | 9/1966 | United Kingdom . |

OTHER PUBLICATIONS

Hodgins and Levy, "Affinity Adsorbent Preparation," Journal of Chromatography, 202 (1980) 381–390.

Churms, *CRC Handbook of Chromatography*, CRC Press (1982) p. 127.

*Primary Examiner*—Cynthia L. Nessler

[57] ABSTRACT

A process and device for separating a mixture of substances by sorption of the components of the mixture on two different sorption agents with independently adjustable sorption properties. The process is characterized in that the mixture of interest is introduced into a gap between two surfaces of sorption agents. A gap medium in which the components of the mixture are soluble and/or dispersible and/or in which they can be evaporated is located between the facing surfaces of the sorption agents (1,2). Of the three different phases consisting of surfaces and gap medium at least two move in different directions at a substantially constant distance apart, and the separated components of the mixture located on the sorption means are extracted after passing through the separating section.

18 Claims, 4 Drawing Sheets

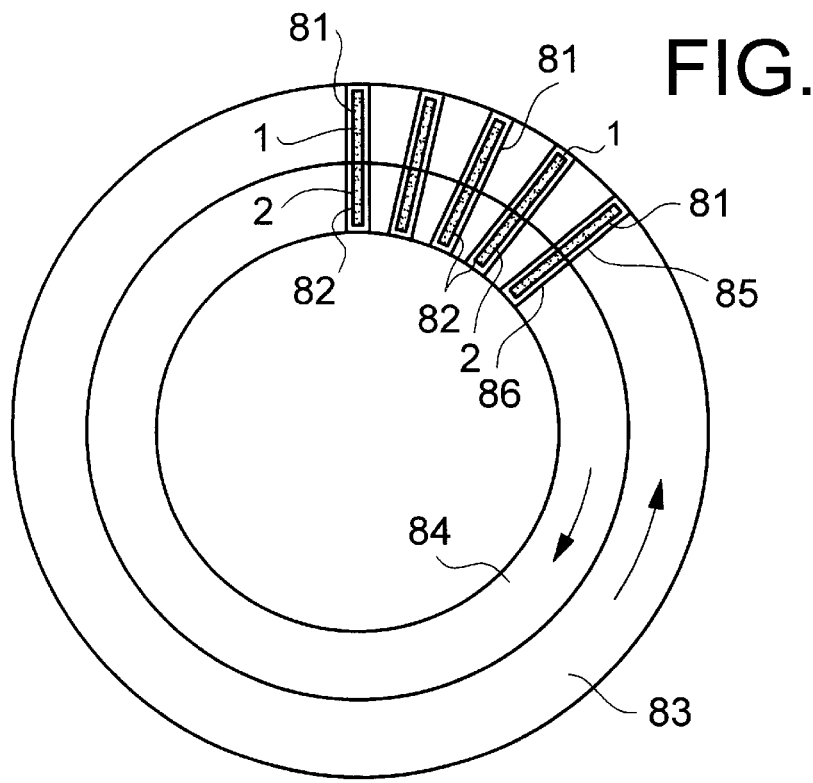
FIG. 8
FIG. 11
FIG. 9
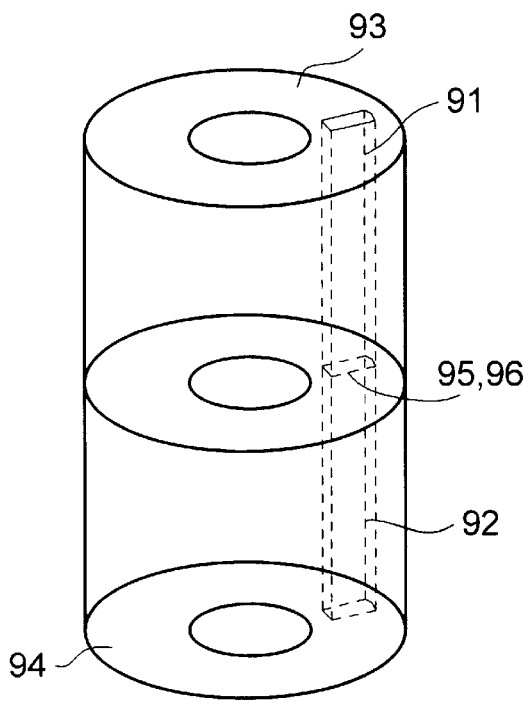
FIG. 10
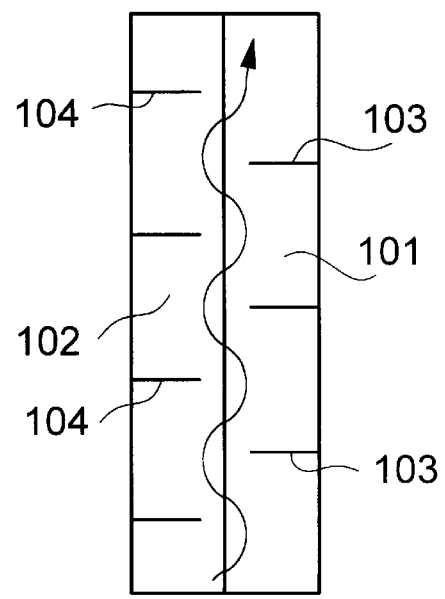

CONTINUOUS CHROMATOGRAPHY

This application is a continuation of application Ser. No. 08/476,057, filed Jun. 7, 1995 now abandoned which is a continuation of application Ser. No. 08/119,082, filed Sep. 16, 1993 now abandoned.

BACKGROUND OF THE INVENTION

The invention concerns a process and a device for continuous chromatography (CC).

The term "chromatography" is generally referred to as a separation process in which substances that are normally distributed between phases due to physical and chemical differences and principles can be separated from one another, monitored by detection processes and recovered by elution. of the phases used in chromatography, one is a non-moving phase (stationary) and has as a rule a large surface, the other is moving (mobile) and passes over or through the stationary phase. The stationary phase can be a solid (adsorbent) or a liquid, whereby in the latter case the non-movability of the phase and its large surface can be obtained by applying the liquid as a thin film to a porous carrier having a small particle size. The mobile phase is, as a rule, a liquid or gas that is not miscible with the stationary phase. Due to these differences one distinguishes in general between liquid-solid chromatography, liquid-liquid chromatography, gas-solid chromatography and gas-liquid chromatography. From principles of separation one can distinguish between adsorption- and distribution-chromatography, whereby separation of mixtures takes place due to differences in the retention of individual components on the stationary phase, whereby the resolution depends upon various factors, particularly upon the different retentions of the individual components on the stationary phase. Since the separation efficiency of a chromatography column depends especially upon the bead size of the stationary phase, (e.g. the size of the surface, peak widening by differing path lengths), one uses in the so-called high performance (or high pressure) liquid chromatography (HPLC) essentially material naving a small particle size (5–30 micron) compared to gel-chromatography (35–75 microns) or column chromatography (120–200 microns); the small particle size of the adsorbent requires the use of high pressure (up to 400 bar).

To carry out the chromatography, a mixture is applied at a location at the beginning (of the column, thin layer, etc.) and is transported by the mobile phase (gas in the case of GC, solvent in the case of HPLC). According to the adsorption/desorption equilibrium the components will pass at differing speeds through or over the stationary phase, whereby the maximum speed will be the speed of the mobile phase.

The chromatography processes known to-date have various disadvantages. For example, continuous operation of such chromatography set-ups is not possible, and an electronically controlled self-optimization is not meaningful or for that matter even possible during the course of the separation process. With similar retention times for various substances, the separation is often incomplete; the coverage of the adsorptive phase during a preparative (laboratory) scale separation (which corresponds to the migration zone of a still unseparated mixture) corresponds as a rule to a local overloading of the stationary phase, e.g. of a column, and the full separation efficiency will be achieved only towards the end, where the substances to separate are already distributed over a larger column area, i.e. are already largely separated; the majority of the adsorptive phase (that which is outside of the migration zone) does not participate at a given moment in the separation.

The distribution always occurs only between an adsorptive medium (stationary phase) and the transport medium (mobile phase), but not between two largely freely selectable adsorption media, as, for example, between adsorption media that are selected according to their physical, chemical and/or chiral properties for good separation of certain substances (as, for example, two enantiomers, different polar, acid/base or opposite (and of adjustable strength) electrically charged sorption media).

In addition to this, the temperature of the stationary phase and the mobile phase are as a matter of course about the same, and can not be set at different temperatures.

SUMMARY AND OBJECTS OF THE INVENTION

The object of the present invention is to avoid the drawbacks associated with the known chromatography processes, to present a chromatography process that is suitable for a continuous process, whereby, in addition, an electronically controlled self-optimization is possible, and to provide a rapid, continuous and good separation due to freely selectable and for specific substances selectively set physical, chemical and/or chiral conditions of the various separation phases, whereby the process is suitable for preparative scale as well as for technical scale separations.

The object is achieved by a process for separating a mixture of substances through sorption of the mixture components on two different sorption agents. More particularly, the invention provides a process for separating components of a mixture of substances by passing the mixture through a separation section of a device where sorption of the components occurs on two different sorption agents, whose sorption properties can be adjusted individually and independently. The process comprises introducing the mixture to be separated into a gap between two moveable surfaces of the sorption agents, wherein the introduction occurs over substantially the entire region perpendicular to the direction of movement of the surfaces of the sorption agents, wherein the gap contains a liquid or gaseous gap medium or vacuum, in which the components of the mixture are soluble or dispersible or in which they can be evaporated, and the two surfaces of the sorption agents move in opposite directions at a substantially constant distance apart. The process further comprises recovering the separated components of the mixture located on the sorption agents after passing through the separation section.

A further object of the invention is to provide a device for carrying out the process according to the invention.

BRIEF DESCRIPTION OF THE DRAWINGS

FIG. 8 provides an overhead view of a device according to the invention and illustrates two concentric cylinders which turn in opposite directions and which have recesses that form chambers;

FIG. 9 provides a perspective view of a further embodiment of a device according to the invention which includes two cylinders above each other provided with chambers;

FIG. 10 provides a slice through illustration of two facing recesses which form chambers of concentrically arranged cylinders in a radial plane;

FIG. 11 provides a cross-sectional view of recesses; and

DETAILED DESCRIPTION OF PREFERRED EMBODIMENTS

Figure 1:
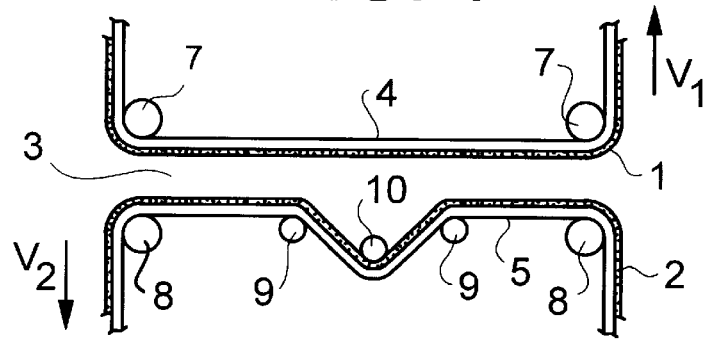
FIG. 1 provides a cross-sectional view of a device according to the invention.

The process according to this invention separates components of a mixture of substances by the sorption of mixture components on two different sorption agents which can be adjusted individually and independently from one another to the mixture at hand according to their sorption properties by suitable choice of charge, polarity, chirality, temperature, cavity size, viscosity, etc. with the individual mixture components binding on those sorption agents with varying strengths due to their different physical-chemical or steric (chiral) properties. The process is characterized in that the mixture to be separated is introduced into the gap between two surfaces of the sorption agents, whereby there is a gap medium in which the mixture components are soluble and/or dispersible and/or in which they can be evaporated located between the facing surfaces of the sorption agents, and of the three different phases consisting of two surfaces of the sorption agents and gap medium at least two phases move in different directions at an essentially constant distance apart, and the separated components of the mixture located on the sorption agents are recovered after passing through the separating section by way of desorption or elution.

Processes are already known for continuous separation of substances that operate according to counter-flow separation process:

According to the so-called extractive distillation, a separation of the mixture to be separated is carried out between an upwards flowing distillate and a liquid film consisting of a mixture of the substances to be separated and extraction solvent running downward on the wall of the distillation column.

According to the so-called falling-film-extraction (distillation) the mixture to be separated runs as a liquid film on the inner wall of a glass tube (for example a distillation column) towards the bottom and is separated through (several) selective evaporation into a rising vapor flow.

According to the so-called counter-flow liquid/liquid extraction, the material to be separated is located in a solvent, through which flows a more dense solvent from above, and in this way a partial extraction of the mixture to be separated is effected.

With all of the known processes that work via counter-flow separation there exists a mobile phase of a liquid that moves by gravity (e.g. a liquid film running on the wall of a distillation column or, in the counterflow liquid/liquid extraction, the more dense solvent percolating through a solution), and a second mobile phase is either a rising steam phase (according to principles of distillation) or a static or rising liquid phase (in a counter-flow liquid/liquid extraction, whereby the solvent phase can be made to rise by means of a pump).

Also, with these processes, all of the disadvantages previously mentioned with normal chromatography processes cannot be avoided. For example, according to these processes the properties of the two phases are only freely and selectively chosen within limited parameters, the flow speed resulting from gravity largely cannot be influenced, and different temperatures between the two phases are not possible or are only possible with difficulty.

In contrast to this, it is easily possible according to the process of the invention to freely choose certain properties such as the type, speed and direction of individual phases, their temperatures, etc. selectively according to the mixture to be separated.

According to the present invention it is possible, for example, to move all phases to be used for separation in freely chosen different directions and with a freely chosen speed, whereby direction and/or speed can be selected for the desired result. In contrast to the state of the art, surfaces of the sorption agents themselves can also be moved with a freely chosen speed and direction, which is not the case in, e.g. a falling-film extraction, i.e. a liquid film flowing over a surface, wherein, moreover, the speed is determined by gravity.

In embodiments of the process according to the invention, the sorption means differentiate themselves according to their polarity, geometric arrangement of binding functions, pore size, viscosity, temperature and/or electric charge. The sorption means (1,2) are preferably on carriers (4,5); they can, e.g. also be various liquid films on carriers (4,5).

In one embodiment of the process of this invention, the carriers (4,5) are flat or curved belts or disks or parts of a cylinder or sphere surface.

In another preferred embodiment the carriers are formed by the walls of recesses, which are located in parallel surfaces, especially in two cylinders which turn in opposite directions and which extend perpendicular to the running direction, in the case of cylinders, parallel to the cylinder axis, whereby the cylinders (cylindrical drums) are arranged concentrically inside each other (with a shared rotational axis) or above each another (with a shared rotational axis and the same base area) and the recesses in the facing surfaces of the cylinders are arranged in such a way that, during the opposite rotational movement of the two cylinders, they are alternately in a position in which their openings are facing each other, and in a position in which their openings are across from a tube wall in which there are no recesses.

If the recesses are on carriers that are flat or curved belts or disks or parts of cylinders or sphere surfaces, e.g. belts that are arranged essentially parallel to each other, preferably, as in the case of cylinders, only the walls of the recesses form the carriers for the sorption agents.

The recesses are formed e.g. as grooves or channels in the form of semicircles, in V-forms or in rectangular cross-sections and have preferably the form of chambers having a rectangular cross-section, whose longitudinal sides are arranged perpendicular to the facing surfaces, whereby the deepness of the chambers can be a multiple of the width of the opening, e.g. 1 to 100 times larger.

The recesses in the facing surfaces, and especially the cylinders are foremost formed such that they are essentially mirror images. The recesses cover essentially the entire length of the cylinder.

The number of recesses that are on the facing surfaces, especially the cylinders, can vary in a broad range and depends particularly upon the length of the separating section or the radius of the cylinder. The number of recesses lies preferably in the range of from 5 to 10000, especially between 20 and 1000, and more preferably between 30 and 100. The distance between two neighboring recesses corresponds at least to the width of the opening of the recess and is preferably bigger than this and is especially 2 to 4 times the width of the opening.

In order to form the largest possible adsorption surface available for separation, the recesses can in addition contain lamina running parallel to the direction of the recesses.

The radius of the cylinders can also vary in a wide range, and is arranged particularly according to the amount of the mixture to be separated, i.e. according to its use in the laboratory, semi-technical (pilot plant) or technical (commercial) scale. As a rule the radius for apparatus in laboratory scale lies in the range from 5 to 30 cm, for semi-technical in the range of from 50 to 300 cm. The height of the cylinders is also particularly dependent upon the amount of mixture to separate; it lies preferably between 5 and 100 cm for laboratory scale and from 50 and 500 cm for semi-technical scale.

The deepness of the recesses, e.g. of the previously mentioned and preferably used chambers, is also variable in a wide range; the recesses can extend from their opening to the facing wall of the cylinder which together forms, so to speak, the border surface for the recess, e.g. the chamber. It is, depending upon the size of the apparatus used, essentially in a range from 0.1 mm to 100 cm, and preferably in a range from 0.1 to 10 cm. The upper end of the range corresponds essentially to the largest thickness of the cylinder, whereby the thickness lies preferably in the range from 0.1 to 50 cm, and preferably from 1 to 20 cm.

The recesses of the facing surfaces, preferably of concentrically arranged tubes, contain preferably flow deflection devices which are arranged at certain distances on the surfaces of the recesses that are parallel to the cylinder axis such that they change the flow direction of the gap medium which is flowing parallel to the cylinder axis such that when the recesses face each other, during the course of flow through the recesses, this medium flows alternately from one recess into the facing recess, whereby as a rule the effectiveness of the separation can be increased. The flow deflection devices are preferably arranged parallel to one another, and consist preferably of (small) plates adapted to the cross-section of the recess that, e.g. with chambers can be rectangular. Preferably the form of the flow deflection devices corresponds to the overall cross-section of the recesses.

The flow of the gap medium through the recesses is produced preferably by means of a suitable circulation system, whereby preferably each individual recess of at least one or both facing surfaces is associated with a circulation system, e.g. a circulation pump.

In addition, the carriers in the form of flat or curved belts or disks or that constitute parts of a cylinder or sphere surface, especially when they have facing surfaces parallel to each other as, for example, belts arranged parallel to each other, are provided where useful, especially for the cylinders, with the previously described recesses, preferably chambers, whereby facing surfaces correspond to facing surfaces of the cylinders. In addition, it is useful if the recesses of these kind of carriers are equipped with a circulation system, e.g. a circulation pump, whereby also here preferably each recess of each or or both carriers is associated with a circulation system.

The distance between the phases that move in different directions is variable in a wide range, whereby optimizations in view of the device and in view of the results are possible. Temperature differences between the individual phases as well as temperature gradients within a phase over the length of the separating section can be easily and freely set, whereby a further optimization of the desired results is possible. In the case of two surfaces with recesses moving in opposite directions, the distance is preferably as small as possible and will only permit the movement in opposite directions.

With the process according to the invention it is also possible to carry out the chromatography in a continuous, two dimensional way, i.e. it can be carried out as an area separation of a mixture. This is possible according to the invention in that at least two of the phases moving in different directions, e.g. two parallel belts, move at an angle between 90° and 180°, whereby the angle of 180° represents movement in opposite direction (e.g. two belts running in opposite directions) and the angle of 90° represents movement in a perpendicular direction (e.g. two belts running perpendicular to one another). In addition the third phase (gap medium) can also move in a direction freely selectable to the other two phases, e.g. as a gas flow flowing in a particular direction, or by means of a movable grid or a similar device positioned between the sorption agent phases (e.g. belts).

A further advantage of the process according to the invention is that the phases are not required to consist of at least one liquid as is the usual case with processes that are based upon countercurrent flow separations, but rather the phases can also be solid, whereby further optimizations are possible, e.g. in view of the type of apparatus to carry out the process.

The separation system according to the invention consists of a three phase system in the normal case, whereby, e.g. the flow direction, speed and/or temperature of each of the three phases is independent of each other and freely selectable and/or adjustable, and can be adapted to the separation problem at hand.

If the length of time of sorption is very short on one of the two surfaces that are moving in different directions and the separated substance is found mainly on the surface of the other sorption agent or in the gap medium, the surface of this sorption agent serves mainly only to set the desired velocity profile in the gap medium, and acts more or less as a rebound wall; in this case the separation system according to the invention can also be seen essentially as a two phase system.

By choice of the direction and speed of the phases, as well as by choice of the other variable parameters, a desired discharge point for the separated fractions can be set. It is determinable through the vectors of quantity and direction of the velocity multiplied by the residence time of the components in or on the three phases, consisting of the surfaces and the gap medium; the introduction point is arranged according to this purpose so that the separating section to be passed is as large as possible.

The sorption agent of the phases according to the invention can be adsorption agents and/or absorption agents. They are differentiated especially according to their polarity, geometric arrangement of binding functions (e.g. chirality), pore size, temperature and/or electric charge.

Such differing parameters are, e.g., in respect of:

the polarity: acid, base, acid and base, aliphatic, aromatic, substituted (e.g. through different polar groups, halogen groups, OH groups);

the geometric arrangement of binding functions: chiral surfaces, enzyme-covered or enzyme-like surfaces, complex forming agents, etc.;

the pore size: use of different zeolites, organic or inorganic polymers (e.g. polystyrol, polyethylene, polyamide, polyurea derivatives, polycarbonic acids, polyesters, polyamines, cellulose derivatives), preferably with different diffusion coefficients; different liquid films, e.g. paraffin oils, silicon oils and others known for liquid films;

temperature: the temperature of the phases can be varied in a wide range, and can be in a range from the freezing point to the boiling point, e.g. in the range of −79° C. (temperature of dry ice) to 200° C., and especially in the range of −10° to 100° C., and especially in the range of 0° to 50° C., whereby in view of having an easy process and running the separation economically, ambient temperature is especially preferred;

electric charge: in addition to opposite charge (+or−) it can have differing strengths. It can also be applied simultaneously with other surface coatings and/or changes if the carrier belt is electrically conductive.

The sorption agents can be fluid films situated on a carrier. According to the invention, the usual sorption agents typical to chromatography and/or electrophoresis are preferably used as sorption agents.

Preferably the sorption means are on a carrier, e.g. on flat or curved belts or discs, or on parts of cylinder or sphere surfaces and/or in the previously described recesses; in the case of two cylinders rotating in opposite directions, the sorption agents are preferably found only on the walls of the recesses. These carriers can then be moved in different directions and when desired with different speeds.

The gap medium between the surfaces of the sorption agents can be a liquid, a gas or a vacuum; in the case of a vacuum, this is limited only be the vapor pressure of the mixture to be separated. The gap medium can also be the mixture to be separated, e.g. a mixture of two or more liquid components. The gap medium can move from the center (introduction point) to one or more discharge points. Preferably the mixture to be separated will be introduced in the middle region of the gap thereby yielding the largest possible separating section in both directions.

The distance between facing surfaces of the sorption agents is variable in a wide range, as is the number and kind of optional recesses; it is limited in that it must be possible that the mixture components are in exchange between the two surfaces of the sorption agents over the gap medium located in the gap. Preferably the distance between the facing surfaces of the sorption agents is adjustable. The distance is, especially in the case of surfaces without recesses, preferably between 0.01 microns and 20000 microns, and especially 0.1 to 2000 microns.

The speed of the sorptio n agents moving in different directions, e.g. of the two sorption agents and the gap medium, or the rotational speed of the cylinders can be th e same or different, and can vary in a wide range. P referably the speed of the sorption agents ranges from 0.1 mm/sec to 500 mm/sec, and the rotational speed ranges from 0.1 revolution per hour to 10 revolutions per minute.

The temperature of the sorption agents or the temperature of the surfaces of the sorption agents can be the same or different; in certain cases it may be useful that the temperature of the sorption agents, at least of their surfaces, is different and/or has a temperature gradient in the direction of the s eparating section.

The gap medium found in the gap between the surfaces of the sorption agents moving in opposite directions can be stationary but can also in some ca ses flow in a desired direction and speed between th e two surfaces of the sorption agents.

The mixture to be se parated can be introduced into the separation system according to the invention using a s uitable device. For this purpose, one can use a "roll-on-system" or a "brush-on-system", or a capillary jet, a desorption/adsorption lock, a fine hose, a frit, a hollow pin, or a pump, or the mixture can be condensed from the vapor phase onto one or both surfaces of the sorption agents, or the mixture to be separated is introduced into the circulation system of one or more of the recesses. The roll-on-system can include, e.g., a moistening hollow pin, the brush-on-system, e.g. a moistening, stiff hollow pin.

The discharge of the components (fractions) of the mixture separated according to the invention can be obtained with a suitable discharge system. Particularly according to the invention, the desorption of the components (fractions) is obtained, e.g. by way of a gas flow whose speed and temperature are preferably adjustable, e.g. through condensation in a cold trap and/or through thermal desorption, e.g. by means of a hot roll located at the back side of the loaded sorption surface; through IR- or microwave radiation, through ultrasound, through elution, through recovering the components from the circulating gas flow or circulating system of one or more recesses, e.g. through a pump, whereby two or more of these possibilities for desorption can be used simultaneously. After discharge, especially through a gas flow or through thermal desorption, precipitation is obtained preferably on a cold collector surface, e.g. in a cold trap.

When the system is provided with recesses and a circulation system, the mixture to be separated can be fed in the circulation system of the introduction recess as a defined, normally at a significantly elevated temperature saturated gas stream (or solvent stream). Correspondingly, the separated substances can be removed and obtained by "tapping" into the discharge circulation systems, e.g. precipitation on a cold collecting surface.

For the running of the process (ascertaining purity of the separated fractions during the process), various suitable, known detection methods can be used. Preferred according to the invention are e.g. IR-absorption (e.g. by means of a IR-diode-array-photometer), VIS- or UV-absorption (e.g. by means of a UV-diode-array-photometer), refractive index (e.g. especially as used in HPLC processes), determination of the optical rotation, determination of the polarizability, of the dielectric constant (dc). Such detection processes are especially useful for an electronically controlled, continuous separation optimization, and the continuous process according to the invention will preferably be carried out such that individual parameters are each varied, resulting changes in the separation are determined and all of the separation parameters are continuously optimized by harmonizing them with each other.

Two or more of the previously mentioned detection processes can be used at the same time.

Separation parameters that can be optimized can be parameters which are fixed by the individual design of the device or continuously optimizable parameters adjustable to the separation problem at hand.

Apparatus-set parameters that can be optimized are, e.g. the length of the separating section, the width of the separation section, the gap width, i.e. the distance between the surfaces of the sorption agents that can be adjustably constructed, sorption characteristics of the separation surfaces, angle between the running direction of the surfaces of the sorption agents (e.g. with the adjustable belts that are loaded with sorption agents) number, form and dimension of the recesses.

Especially suitable parameters for a particular separation problem are e.g.: the temperatures $T_1$ and $T_2$ of the two sorption agents/surfaces of the sorption agents, and/or the temperature gradients of $T_1$ and $T_2$ along the separating section 1, the (ultra)sound intensity on the separation surfaces (by which the rate of exchange of the components to be separated on the sorption means can be influenced), pressure (which can be varied in a wide range, from vacuum to excess pressure, e.g. super critical pressure) speed of the surface 1 ($V_1$) and/or the speed of facing surface 2 ($V_2$), or the rotation speeds of the cylinders that are turning in opposite directions, the amount of mixture introduced and/or the time of introduction (e.g. by the optimization of the feed of the mixture to be separated), flow speed and/or flow direction of an additional carrier flow to discharge non-migrating substances, the kind and strength of an electric charge on the surfaces of the sorption agents.

In addition, it is possible to combine two or more of the previously mentioned optimization parameters.

According to the process according to the invention, at least two phases move in different directions, and in the case of parallel flat surfaces, e.g. belts, preferably at an angle to each other between 90° and 180°, i.e. the direction of movement of the two phases form an angle between 90° and 180°.

In view of the design of an apparatus to carry out the process, preferred are angles of 180° and 90°, i.e. those embodiments in which at least two of the phases, e.g. in the form of sorption agents on belts, move oppositely (180°) or perpendicularly (90°) to one another.

The process according to the invention can be carried out generally in a vacuum, at atmospheric pressure or at a raised pressure, e.g. supercritical pressure, whereby the pressure is chosen according to the separation problem at hand.

According to the continuous chromatography (cc) process according to the invention, a mixture is separated in two fractions, each of which still can contain a mixture of components. For further separation and/or purification of these fractions (components) of the mixture obtained according to this separation operation, the process can be repeated for one or more of the fractions (components) obtained as often as desired.

The device according to the invention for carrying out the process according to the invention for continuous chromatography of a mixture encompasses two differing sorption agents (1,2) and a gap (3), in which is found the gap medium in which the mixture components are soluble and/or dispersible and/or in which they can be evaporated, whereby the sorption agents (1,2) are arranged so that at least two of the three phases consisting of the sorption agents (1,2) and the gap medium located in the gap (3) move in different directions at an substantially constant distance from one another, as well as an application device (10) for introduction of the mixture to be separated and a discharge device for removing by desorption or elution the separated fractions of the mixture after passing through a certain separating section.

Embodiments of the apparatus according to the present invention are already described in conjunction with the process for carrying out the invention.

The temperature of the sorption agents (1,2) can vary and/or a temperature gradient can be present along each separating section (1) of the sorption agents (1,2).

Also, the gap medium of the gap (3) can be freely chosen to flow at a determined speed and direction between the two surfaces of the sorption agents (1,2) as required.

Introduction of the mixture to be separated is accomplished using a suitable introduction device (introduction system (10)). Preferably the introduction system is a roll-on-system (e.g. in the form of a moistening hollow pin (10)), or a brush-on-system (e.g. in the form of a moistening, stiff hollow pin (10)), or a capillary jet, a thin (capillary) tube, a frit, a hollow pin, a device for feeding a defined saturated gas flow, especially for feeding in the circulating system of one or more recesses, or a desorption/adsorption lock. The mixture to be separated can also be introduced by condensation of vapor on one or both surfaces of the sorption agents (1,2) using a suitable vaporizing device.

In addition, the apparatus according to the invention encompasses suitable discharge devices to remove the separated fractions (components) of the mixture after a determined separating section has been passed (section between the introduction point and the discharge point, 1). Preferably the discharge devices are based on a gas flow that is adjustable in speed and/or temperature, e.g. produced by the gas flow of a circulation system of one or more recesses, and/or means for thermal desorption, e.g. by means of a hot roll located at the back side of the loaded sorption surface, or by means of a set-up for microwave radiation or IR-radiation, and/or means for ultrasound or for elution, and/or a pump. In case of a discharge with a gas flow or in case of a thermal desorption, which is preferably is used a precipitating device based on a cold collecting surface, e.g. a cold trap.

With surfaces having recesses, especially in the case of cylinders, a suitable pump as an introduction and discharge device is used.

The apparatus of the present invention may also contain a means for detecting the separated fractions (components), which is particularly useful when the separation is electronically controlled and constantly optimized.

Such detection devices which are in one or more positions of the separating section or separation surface in suitable distance and arrangement to the sorption agents, or also can be placed after a desorption device are especially such devices that measure the IR absorption of the fraction, e.g. an IR-diode-array-photometer, or the VIS- or UV-absorption (e.g. a UV-diode-array-photometer, or the refraction index, the optical activity, the polarizability or the dielectric constant (dc).

The device according to the present invention can also be provided with two or more of the previously mentioned desorption and/or detection devices. Preferably the device is equipped such that it can be operated in vacuum, at atmospheric pressure or at elevated pressure, depending upon the mixture to be separated, e.g. super critical pressure of the mixture components, as well as in a wide temperature range, especially in conjunction with the previously mentioned preferred ranges for carrying out the process. Further embodiments of the apparatus according to the invention are previously described in connection with the way of carrying out the process.

In case of essentially parallel arranged flat surfaces of the sorption agents, the direction of movement of at least two of three different phases (sorption agents 1,2; gap medium in the gap 3) in an embodiment of the device according to the invention form together an angle between 90° and 180°.

Particularly useful is an angle of 180° and one of 90°; in these cases the phases, e.g. the sorption agents applied to belts, move countercurrently (180°) or perpendicularly (90°) to one another.

Below, with reference to the drawings, are described exemplary embodiments, to which the instant invention should not be limited.

FIG. 1 shows a cross-sectional view of a device according to the invention. The sorption agents 1 and 2 are on belt-shaped carriers 4 and 5, which may be made of plastic or metal. The belts 4 and 5 and therewith the sorption agents 1 and 2, move over driving rolls 7, 8 in opposite directions, i.e. their direction of movement forms an angle of 180°. The belt 5 with sorption agent 2 runs also over the deflection rolls 9 over a roll-on-system or brush-on-system 10 for introduction of the mixture to be separated. Between the surfaces of the sorption agents 1 and 2 is found the gap 3, in which is found the gap medium. The belts 4 and 5 move with velocity $V_1$ and $V_2$.

Figure 2:
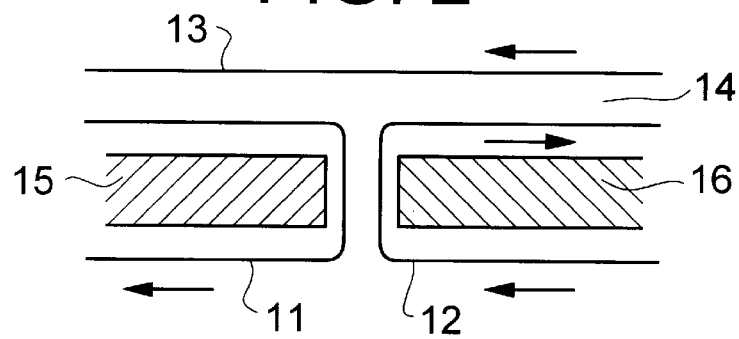
FIG. 2 provides a cross-sectional view of an introduction device in the form of a desorption/adsorption lock.

FIG. 2 is a schematic representation of an application device according to the invention in the form of a desorption/adsorption lock. The two belts 11 and 12 are found in the area of the heating devices 15, 16 and are at 2 different temperatures $T_1$ (belt 11) and $T_2$ (belt 12), whereby $T_1 > T_2$. A sample is on belt 11, which due to the different temperatures of the two belts, is desorbed from belt 11 and adsorbed by belt 12. The deflection rolls for belts 11 and 12 are not indicated. Belt 13 forms one of two phases which move in different directions, e.g. a belt as carrier which is coated with a sorption-agent and the other two phases being belts 11 and 12 which are also coated with a sorption agent. The application of the mixture to be separated occurs on the outer side of belt 12. The gap 14 with gap medium is located between belts 11 and 12 and belt 13.

Figure 3:
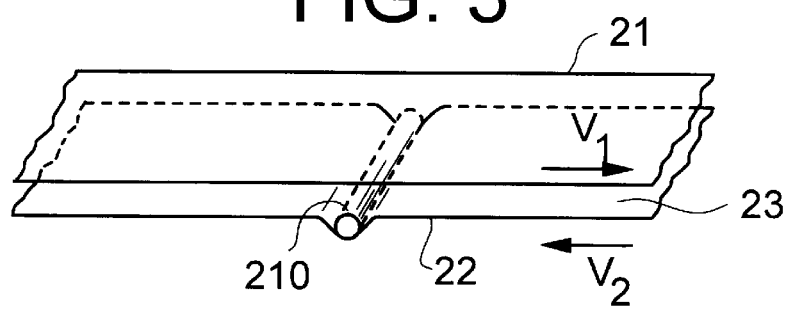
FIG. 3 provides a perspective view of a device according to the invention.

FIG. 3 shows a device according to the invention in a perspective view. The belts 21 and 22, which move in opposite directions, form the two phases with different directions of movement. They are, for example, plastic or metal belts that are coated with a sorption agent, whereby the surfaces of the sorption agent coatings face each other. The gap medium is found in gap 23. The introduction of the mixture to be separated occurs through the introduction device 210, which is a wetting hollow pin. The two belts 21 and 22 move at velocities $V_1$ and $V_2$, which can be different. Belt 21 can also be stationary, i.e. can be formed as a non-moving wall; in this case occurs, e.g. a movement of the gap medium in the opposite direction. The deflection rolls and transport rolls are not indicated. The discharge occurs after a determined separating section (distance between the point of introduction and the point of discharge) in both belt directions.

Figure 4:
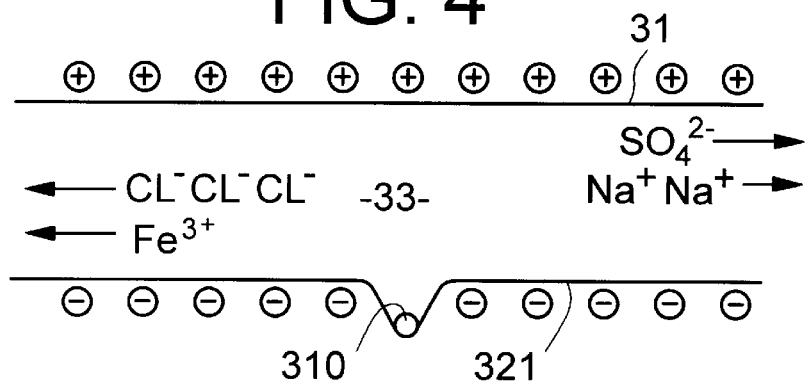
FIG. 4 provides a cross-sectional view of the device illustrated in FIG. 3.

FIG. 4 shows a cross-sectional view of a device of the invention according to FIG. 3. The belts 31 and 32 form both phases which move in different directions; they are arranged so as to serve as charge carriers for opposite, adjustable charges (e.g. metal belts in contact, with suitable charge conveyance), which is illustrated with the indicated+and− charges. In gap 33 is a solvent of various ions flowing through the introduction device 310 (e.g. a porous hollow pin) which shall be illustrated by the introduced kinds of ions.

Figure 5:
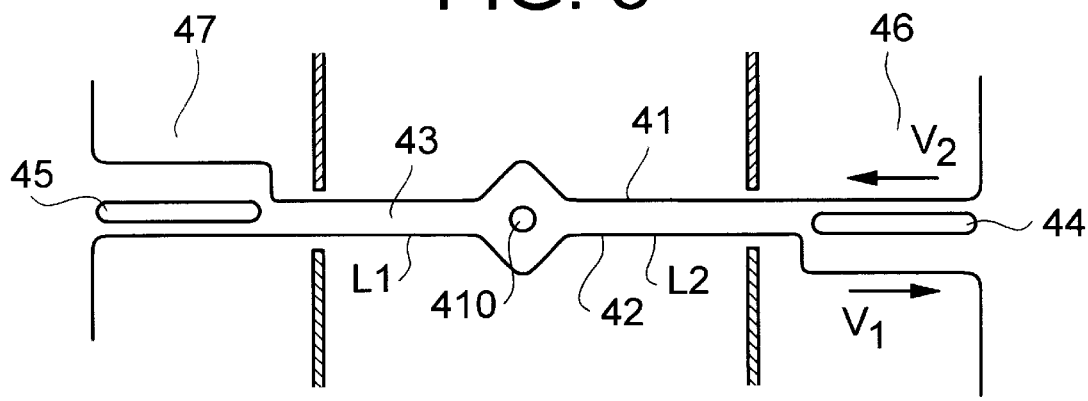
FIG. 5 provides a cross-sectional view of a further embodiment of the invention.

FIG. 5 is a cross-sectional view of a device according to the invention. The belts 41 and 42 form the two phases which move in different directions, and are, e.g. of sorption agent-coated plastic or metal belts. By way of introduction means 410, e.g. in the form of a capillary jet, the mixture to be separated is introduced. At the end of the separating section 1, which is composed of the separating sections 11 and 12, are found the two condensers 44 and 45 for discharge of the separated fractions (components). The fractions are removed at these cooled condensers (e.g. frit-canal-cooler). The gap 43 with gap medium is found between belts 41 and 42. The transport rolls and deflection rolls required for driving the belts are not shown.

Figure 6:
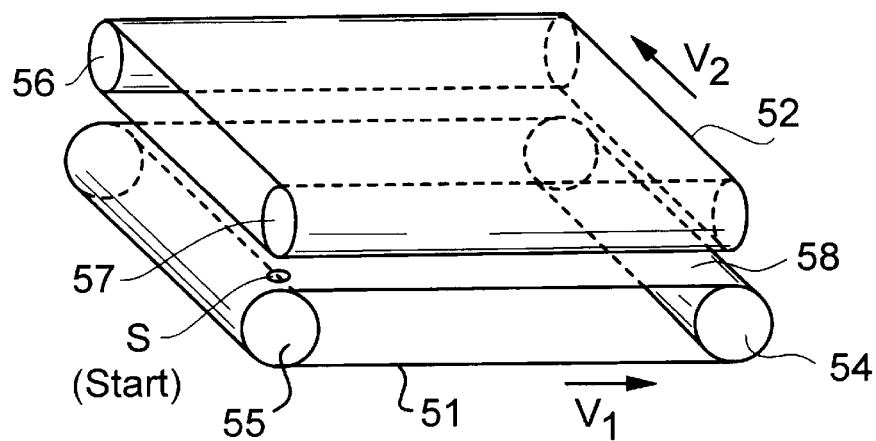
FIG. 6 provides a perspective view of a further embodiment of the invention.

FIG. 6 shows a perspective view of a device according to the invention for two dimensional separation. The belts 51 and 52 form, in a rotational configuration, both phases which move in different directions of the separation system according to the invention, and are, e.g. plastic or metal belts coated with sorption agent. They run over transport rolls 54 and 55, 56 and 57, and their directions of movement form a 900 angle, i.e. both belts 51 and 52 move perpendicularly to each other. Between them is found the gap 58, in which is found the gap medium. The introduction of the mixture to be separated occurs at the position "S" (start). Both belts 51 and 52 form in overhead view a square and congruent outline.

Figure 7:
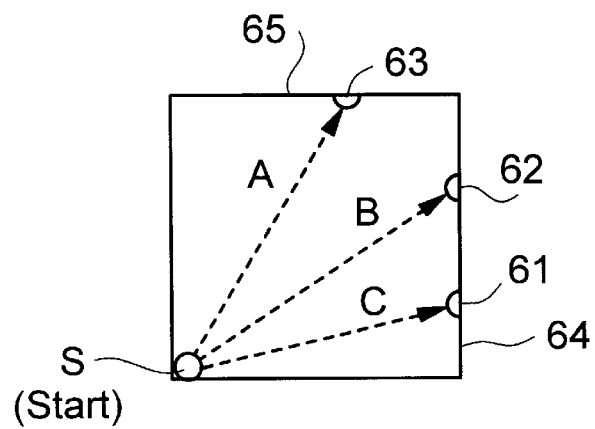
FIG. 7 exemplifies a separation pattern which can be obtained using a device like that illustrated by FIG. 6.

FIG. 7 shows a separation pattern obtained by a device according to FIG. 6 for the fractions A, B and C. The discharge points 61, 62 and 63 for the fractions A, B and C are determined by vectors of the velocity at which the belts 51 and 52 move, and the residence times of the components in the three phases (those formed from the belts 51 and 52 and that of the gap medium in gap 58). It can be useful for the two dimensional separation carried out by a device according to FIG. 6 that the belt speed of bands 51 and 52 are the same. The discharge of fractions A, B and C can occur at the discharge points 61, 62 and 63 along the edges 64 and 65.

FIG. 8 shows an overhead view of a device according to the invention, that includes two concentrically arranged cylinders 83 and 84, which are provided with chambers 81, 82, which are regularly arranged over the entire circumference of the cylinders (of which only a portion is shown); the chamber-forming recesses 81, 82 contain the sorption agent coatings 1 and 2; the arrows indicate the different turning directions.

FIG. 9 shows a perspective view of an embodiment according to the invention, that includes two cylinders 93 and 94 arranged above each other, that contain chambers 91, 92 over their entire circumference (for the purpose of clarity, only one chamber 91, 92 of each cylinder is shown), and in the indicated position their openings 95, 96 are aligned.

FIG. 10 shows a cross-section in a radial plane of two chamber-forming recesses 101, 102 of concentrically inside each other arranged cylinders; the chambers 101 and 102 are equipped with deflection devices 103, 104 in the form of parallel-arranged plates; the arrow shows the change in the flow direction of the gap medium.

FIG. 11 shows a chamber-forming recess 111.

Figure 12:
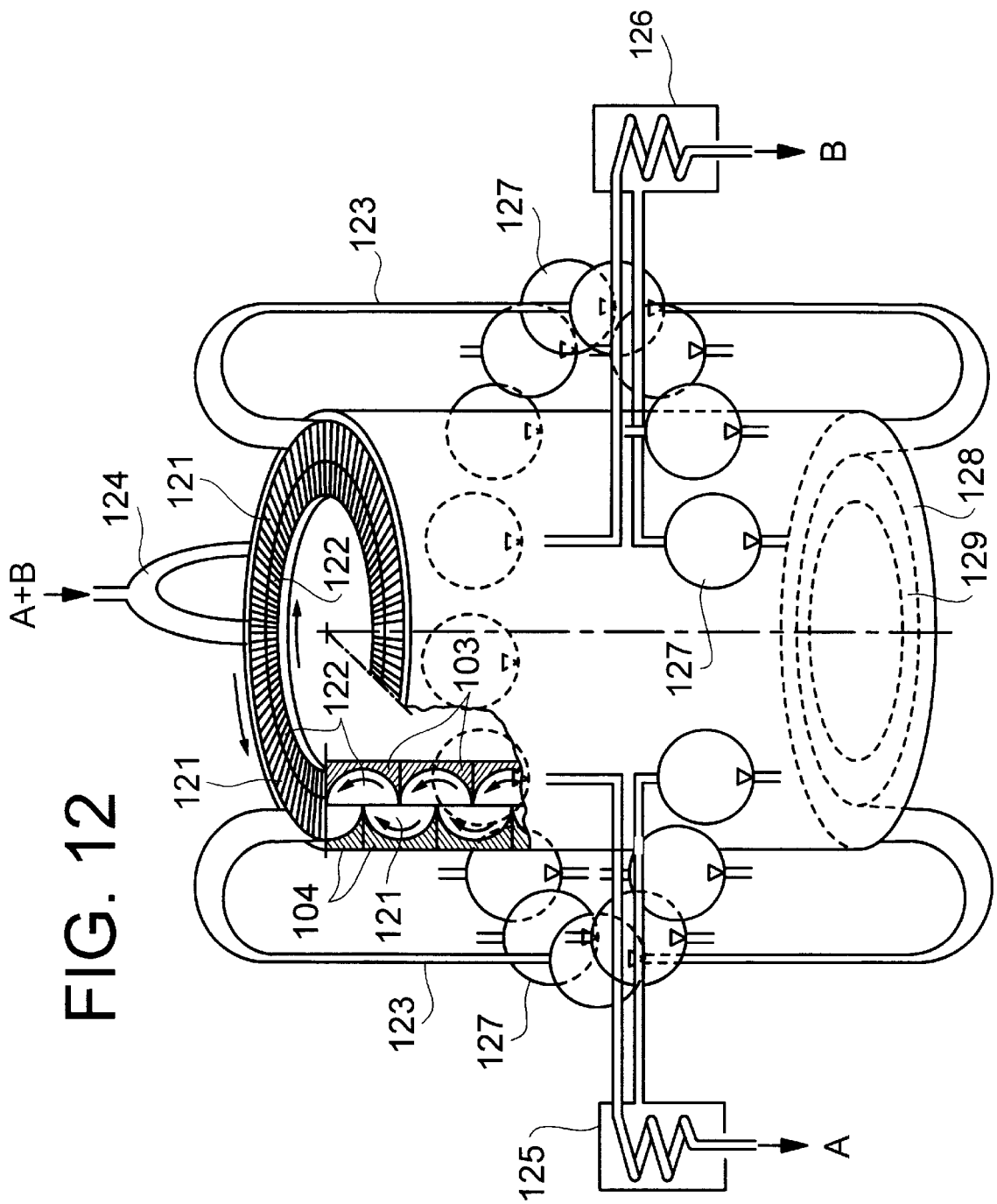
FIG. 12 provides a perspective view of a device according to the invention that includes two concentric cylinders provided with chambers, as well as circulation devices for the chambers and application and discharge devices.

FIG. 12 shows a perspective view of an embodiment of the invention, that includes two concentrically arranged cylinder pipes 128, 129 inside each other with chambers 121, 122; FIG. 12 shows also an introduction system 124 for introducing the mixture A+B to be separated, as well as discharge systems 125 and 126 for capturing components A and B; in addition is indicated a circulation system 123 that is associated with the chambers 121, 122, and which is equipped with a circulation device (circulation pump) 127; for the other chambers only the circulation devices (circulation pumps) (127) for the circulation systems are shown.

The exposed portion shows a partial cross-section of chambers 121, 122, which are equipped with flow deflection devices 103, 104; the arrow indicates the direction of flow of the gap medium through the chambers 121, 122.

EXAMPLES

Example 1 a. Using a device according to either FIG. 1 or FIG. 3, a mixture to be separated is introduced continuously by way of introduction device 10, 210 in the gap 3, 23 between the two belts 4, 5; 21, 22 which move in opposite direction at speeds $V_1$ and $V_2$ and which are coated with sorption agents 1, 2. The distance d between the facing surfaces of the sorption agents is <10 mm. The starting line S is found approximately in the middle of the separating section 1, so that the substance has to pass approximately equal distances to each end of the separation system. The gap between the surfaces of the sorption agents (the gap 3, 23) can be completely filled with a liquid mixture to be separated, or only the walls of the gap may be covered with a gas pressure p in the gap.

If the mixture consists of several different substances that have a preference to adsorb onto one or the other of the surfaces of the sorption agents and in addition a rapidly occurring exchange of the molecules guarantees that thermodynamic equilibrium is reached, the substances will have a preference to migrate in one direction or another. The sharpness of the separation or the separation performance will be determined by the energy difference of the possibilities for sorption, the temperature of the system, the position exchange rate, the belt speed and the distance traveled by diffusion or convection during the residence time in the gap medium. The separation system is controllable, then, especially through the choice of sorption materials and the parameters $T_1$, $T_2$, $V_1$, $V_2$, d, l, p and the amount of mixture introduced.

By an additional supply of carrier gas or carrier liquid to the gap 3, 23 in the direction of the belt or cross-wise thereto, non- or only slowly-migrating components of a mixture can be discharged at both ends without a preferred direction or cross-wise thereto.

b. Multicomponent separation

If the above-described direction of the oppositely running belts (angle of movement direction of 180°) is changed from 180° to other angles, e.g. using the device according to FIG. 6 with an angle of 90°, further separate fractions can be discharged along the edges 64, 65 of the separation pattern of FIG. 7. The mixture to be separated is, in this case, applied in the shape of a point at the position S (start). In this way multicomponent mixtures can be separated in a continuous process.

Example 2 a. Separation of a dye-stuff mixture having dye-stuffs of different polarities.

Using a device according to FIG. 3 a mixture to be separated, as a gas, liquid or solid, is introduced by way of application device 210 in the gap 23 between the belts 21 and 22 (e.g. as a solution and subsequent evaporation of the solvent, by condensation from a vapor phase, etc.). Plastic- or metal-belts can be used that are coated with typical chromatography sorption agents. The surfaces of the sorption agents demonstrate different surface polarity. By variation of the belt speed, temperatures of the sorption agents etc. each separation can be optimized.

b. Separation of different polar, non-ionic substances

The procedure of part a., above, is followed with the exception that the polarity or the difference in polarities between the sorption agents is set by an adjustable electrical tension applied to the metal belts 21 and 22. The metal belt surfaces can also be coated with inert materials such as graphite, TeflonR, polyethylene, polyamide, metal oxides, etc.

A separation of the mixtures mentioned in parts a. and b. can be achieved advantageously and effectively using a device according to FIG. 12, in which chamber walls are coated with sorption agents of differing surface polarity (as in part a.) or the polarity or difference in polarities of the sorption agents is set by an adjustable electrical tension applied to the chamber walls of the cylinder pipes (as in part b.).

c. Separation of multiply charged ions from singly charged ions

A device according to FIGS. 3 and 4 is used. An aqueous solution of singly and multiply charged ions of the same charge is introduced in the separation system by way of application device 210, 310 in gap 23, 33. An adjustable charge applied to belts 21, 22 and 31, 32 causes adsorption of the different ions on the walls with varying strengths, dependent upon the charge number of the ion. The singly charged ions migrate against the belt direction (with opposite charge) and thereby create a largely electrical neutrality of the separated fractions. Because the system works without gas, the flow of fluid is adjusted directly by the introduced flow. The purity can be ascertained e.g. by the optical rotation or the dielectric constant (dc) of the single fractions.

To adjust and optimize the separation process, the following parameters can be set or changed:

1. pH of the mixture
2. Ion strength of the mixture
3. Temperatures $T_1$ and $T_2$
4. The tension $U_1$ and $U_2$ of the belts 21, 31 and 22, 32 (adjustment of the electric field)
5. Distance between walls (adjustment of the electric field and/or turbulence)
6. Belt speed (adjustment of the separation sharpness, turbulence).

As mixture to be separated can be used:

a. multiple, like-charged anionic and cationic dyestuffs in water
b. $Fe^{3+}$, $Na^+$, $Cl^-$, $SO_4^{2-}$ →$FeCl_3$ and $Na_2SO_4$ d. Separation of salt solutions in anions and cations ("charged liquids")

A device according to FIG. 3 and 4 is used. A tension is applied to belts 21, 31 and 22, 32, that is a little smaller than the tension for hydrolysis. A diluted or concentrated aqueous solution of KCl is introduced continuously in the gap 23, 33. An excess of anions is transported by the positively charged belt, and an excess of cations is transported by the negatively charged belt. The charge density of the so-obtained "Ionically charged liquid" can be increased considerably by extensive evaporation of the water.

Example 3

Distillation CC or Sublimation CC

A device according to FIG. 5 is used.

The solid or liquid mixture to be separated is introduced in the system by way of introduction device 410. only the facing surfaces of the belts 41 and 41 are covered with the solid or liquid substance to be separated, and a gas pressure p is present in the gap 43. The oppositely moving surfaces have different temperatures $T_1$ and $T_2$. The warmer surface moves at at a higher speed. The gas phase on average thereby moves in the direction of this surface, and easier evaporatable substances migrate in this direction, while lower volatile (dissolved, fluid or solid substances) migrate in the opposite direction.

The mixture is separated into higher and lower boiling fractions by corresponding adjustment of the temperature and speed differences of the walls. Using a raised temperature at the ends of the separating section, the fractions can be quantitatively recovered on cooled condensers 44, 45. The condensate can be discharged using a slight vacuum.

To adjust and optimize the separation process, the following parameters can be set or changed:

1. Amount of substance introduced per time (adjustment of the mixture feed) (ml/min)
2. Temperatures $T_1$, $T_2$ (oC); optionally the temperature gradient along the separating section 1
3. Gas pressure in gap p (torr)
4. Distance been walls (mm)
5. Belt speed $V_1$ and $V_2$ (cm/sec)
6. Partial separating sections $l_1$, $l_2$ (cm)
7. Belt width b (cm)
8. Desorption temperatures $T_3$, $T_4$, $T_5$ (°C.) in the temperature sections 46 and 47 and in the coolers 44, 45
9. Discharge pressure p1, p2 (torr)

As a mixture to be separated, a mixture of ethylene glycol (boiling point =198° C., dc=37.7 (25°C.)) and propylene glycol (boiling point=188° C., dc=32.0(20°C.)) in a 50:50 ratio.

For carrying out the separation process, the above-mentioned parameters can be set as follows:

1. 1,
2. $T_1$=50, $T_2$ =60
3. p=15 or 760
4. <5
5. V1=1, $V_2$=10
6. $l_1$=1, $l_2$=50
7. b=30
8. $T_3$, $T_4$ =100, $T_5$ =20
9. $p_1$, $p_2$=750

Example 4

CC-enantiomer separation

An apparatus according to FIG. 12 is used. The facing surfaces of the cylinders (128) and (129) have differing chirality, but identical temperature. The separation is obtained by selective adsorption of the enantiomers on the surfaces of differing chirality. The enantiomer mixture is introduced in the separation system by means of an introduction device (124).

For adjustment and optimization of the separation process, the following parameters can be set or adjusted:

1. Degree of charge of the chiral surfaces,
2. Temperature of the system
3. Speed of circulation in the circulation systems
4. Rotational speed of the cylinders 128, 129.

As the mixture to be separated, e.g. D,L-lactic-acid can be used.

In an analogous way to example 4, a device according to FIG. 12 and the corresponding sorption agents can be used to separate the mixture of example 3.

Example 5

Multicomponent separation (two dimensional cc)

A device according to FIG. 6 is used.

A multi-component mixture is continuously introduced on a small surface (largely in the shape of a point) at introduction point S (start). The separated fractions can be removed along the edges 64 and 65 (cf. FIG. 7), depending upon their residence time on the surface of belts 51 and 52 and the speed of belts 51 and 52.

For adjustment and optimization of the separation process, the following parameters can be set or changed:

1. Angle between the direction of movement of the belts 51 and 52,
2. relative and absolute belt speed $V_1$, $V_2$ (effect on introduction point, separation performance, separation capacity),
3. as well as further parameters named in the previous examples for regulation and optimization of the separation process.

I claim:

1. A process for separating components of a mixture of substances by passing the mixture through a separating section of a device where sorption of the components of the mixture occurs on the surfaces of two different sorption agents, whose sorption properties can be adjusted individually and independently, and wherein there is an exchange of the components of the mixture between the surfaces of the two different sorption agents, said process comprising introducing the mixture to be separated into a gap between two moveable surfaces of the sorption agents, wherein the mixture is introduced by a conduit means extending substantially across the width of the sorption agents so that the introduction occurs over substantially the entire region perpendicular to the direction of movement of the surfaces of the sorption agents and substantially in one plane perpendicular to the direction of movement of the surfaces of the sorption agents, wherein the gap contains a liquid or gaseous gap medium or vacuum, in which the components of the mixture are soluble or dispersible or in which they can be evaporated, and the two surfaces of the sorption agents move in opposite directions at a substantially constant distance apart, and recovering the separated components of the mixture located on the surfaces of the sorption agents after passing through the separating section.

2. A process according to claim 1, wherein the temperature of the sorption agents are different or a temperature gradient is present in the direction of the separating section.

3. A continuous process according to claim 1, comprising varying individual parameters, determining resulting changes in separation, and continuously optimizing separation parameters by harmonizing them with each other.

4. A process according to claim 3, wherein analysis is carried out by measuring at least one of the infrared absorption, the refractive index, the amount of optical rotation, the ultraviolet absorption, the polarizability and the dielectric constant.

5. A process according to claim 1, wherein the sorption agents are different with respect to at least one of their polarity, geometrical arrangement of binding functions, pore size, viscosity, temperature and electrical charge.

6. A process according to claim 5, wherein the sorption agents are located on carriers.

7. A process according to claim 6, wherein the carriers are flat or curved belts or disks or parts of a cylinder or sphere surface.

8. A process according to claim 6, wherein the carriers are formed by the walls of recesses located in two cylinders which turn in opposite directions and which extend parallel to the cylinder axis, wherein the cylinders are arranged concentrically inside each other, with a shared rotational axis, or above each other, with a shared rotational axis and the same base area, and the recesses in the facing surfaces of the cylinders are arranged in such a way that, during the opposite rotational movement of the two cylinders, they are alternatively in a position in which the recesses are facing each other, and in a position in which the recesses are across from a cylinder wall in which there are no recesses.

9. A process according to claim 8, wherein the recesses of the cylinders arranged concentrically inside each other, contain flow deflection devices, which are arranged at certain distances on the surfaces of the recesses that are parallel to the cylinder axis such that they change the flow direction of a gap medium which is flowing parallel to the cylinder axis such that, when the recesses face each other during the course of flowing through the recesses, this medium flows alternately from one recess into the facing recess.

10. A process according to claim 9, wherein the flow of the gap medium is produced by a circulation system, wherein each individual recess of at least one or both facing surfaces is associated with said circulation system.

11. A device for separating components of a mixture of substances into separated fractions by means of passing the mixture through a separating section thereof where sorption of the components of the mixture occurs on the surfaces of two different sorption agents, whose sorption properties can be adjusted individually, and wherein there is an exchange of the components of the mixture between the surfaces of the two different sorption agents, said device comprising two different sorption agents and a gap between the two surfaces of the sorption agents, containing a liquid or gaseous gap medium or vacuum in which the mixture components are soluble or dispersible or in which they can be evaporated, wherein said device defines means for moving the two surfaces of the sorption agents in opposite directions at a substantially constant distance apart, said device further comprising conduit means extending substantially across the width of the sorption agents for introducing the mixture to be separated into the gap or onto the sorption agents over substantially the entire region perpendicular to the direction of movement of the surfaces of the sorption agents and substantially in one plane perpendicular to the direction of movement of the surfaces of the sorption agents, and a discharge device to recover the separated fractions of the mixture by means of desorption of elution after passage through the separating section.

12. A device according to claim 11, containing devices to detect the separated fractions, which detection devices are located at one or more places in the separating section or separation surface at a suitable distance and arrangement from the sorption agents, or are located subsequent to said discharge device.

13. A device according to claim 1, wherein the detection device is a device for measuring at least one of the infrared adsorption, the refractive index, the amount of optical rotation, the ultraviolet adsorption, the polarizability and the dielectric constant.

14. A device according to claim 11, wherein the sorption agents are applied onto carriers.

15. A device according to claim 14, wherein the carriers are flat or curved belts or disks or part of a cylinder or sphere surface.

16. A device according to claim 14, wherein the carriers are formed by the walls of recesses located in two cylinders which turn in opposite directions and which extend parallel to the cylinder axis, wherein the cylinders are arranged concentrically inside each other with a shared rotational axis or above each other with a shared rotational axis and the same base area, and the arrangement of the recesses in the facing surfaces defines means for placing the recesses, during the opposite rotational movement of the two cylinders, alternatively in a position in which the recesses are facing each other, and in a position in which the recesses are across from a cylinder wall in which there are no recesses.

17. A device according to claim 16, wherein the recesses contain flow deflection devices, said flow deflection devices defining means for changing the flow direction of a gap medium flowing through said gap such that, when the recesses face each other, said gap medium flows alternately from one recess into the facing recess.

18. A device according to claim 17, comprising a plurality of circulation systems to produce flow of the gap medium wherein each individual recess of at least one or both facing surfaces is associated with one of said circulation systems.

* * * * *